United States Patent [19]

Goi et al.

[11] 4,226,941
[45] Oct. 7, 1980

[54] PROCESS FOR THE OPTICAL RESOLUTION OF D,L-2-AMINO-4-METHYLPHOS-PHINOBUTYRIC ACID

[75] Inventors: Hitoshi Goi, Chiba; Shinji Miyado; Takashi Shomura, both of Yokohama; Akira Suzuki, Tokyo; Tomizo Niwa; Yujiro Yamada, both of Yokohama, all of Japan

[73] Assignee: Meiji Seika Kaisha, Ltd., Tokyo, Japan

[21] Appl. No.: 79,366

[22] Filed: Sep. 27, 1979

[51] Int. Cl.³ ............................................. C07B 19/02
[52] U.S. Cl. .................................................... 435/280
[58] Field of Search ................................ 435/106, 280

[56] References Cited

U.S. PATENT DOCUMENTS

| | | | |
|---|---|---|---|
| 3,347,752 | 10/1967 | Rauenbusch | 435/280 |
| 3,386,888 | 6/1968 | Chibata | 435/280 |
| 3,527,671 | 9/1970 | Zenk | 435/280 |
| 3,669,837 | 6/1972 | Parcell | 435/280 |
| 3,816,254 | 6/1974 | Chibata | 435/280 |
| 3,841,966 | 10/1974 | Soichiro | 435/280 |
| 3,963,573 | 6/1976 | Stauffer | 435/280 |

OTHER PUBLICATIONS

Karger, An Introduction to Separation Science, Wiley, New York, 1973, pp. 552–554.

Primary Examiner—Ernest G. Therkorn
Attorney, Agent, or Firm—Larson, Taylor and Hinds

[57] ABSTRACT

L-2-Amino-4-methylphosphinobutyric acid (L-MPGA) which is useful as bactericide and herbicide can be prepared by optical resolution of its racemic mixture, D,L-MPGA with the action of a microbial acylase. The process comprises providing D,L-MPGA in the form of its N-acyl derivative, reacting N-acyl-D,L-MPGA in an aqueous medium with a microbial acylase having an optically specific hydrolytic activity, whereby selectively eliminating the acyl group of N-acyl-L-MPGA to give a mixture of L-MPGA and N-acyl-D-MPGA and isolating L-MPGA from the mixture. The acylase is produced by cultivating a microbial strain belonging to the genus Pseudomonas, Streptomyces or Aspergillus, particularly *Pseudomonas maltophilia* BN-233, *Streptomyces violascens* SF 2072, *Streptomyces diastatochromogenes* SF 2073, *Aspergillus* sp. KS-101 or *Aspergillus* sp. KS-102.

15 Claims, No Drawings

PROCESS FOR THE OPTICAL RESOLUTION OF D,L-2-AMINO-4-METHYLPHOSPHINOBUTYRIC ACID

SUMMARY OF THE INVENTION

The present invention relates to a process for the optical resolution of D,L-2-amino-4-methylphosphinobutyric acid to yield L-2-amino-4-methylphosphinobutyric acid as the desired product.

BACKGROUND OF THE INVENTION

D,L-2-amino-4-methylphosphinobutyric acid (hereinafter referred to as D,L-MPGA) and a salt thereof with an inorganic or organic base are useful not only as bactericides for agricultural and horticultural purposes (Japanese Patent Prepublications Nos. 14644/74, 14641/74 and 26430/74), but also as herbicides, particularly those for perennial weeds and miscellaneous shrubs (Japanese Patent Prepublication No. 139727/77).

A recent study on the herbicidal activity of the compounds has shown that the activity of L-MPGA is about twice as high as that of the racemic, i.e. D,L-MPGA, thus clarifying that the herbicidal nature of the compounds is essentially attributable to L-MPGA and not to D-MPGA.

It has already been proposed to prepare L-MPGA from a known antimicrobial agent, SF-1293 substance, that is L-MPGA-alanyl-alanine by an acid decomposition (Japanese Patent Prepublication No. 85538/73) or by an enzymatic decomposition (Japanese Patent Prepublication No. 31890/74). With respect to SF-1293 substance and its preparation, reference is made to Japanese Patent Prepublication No. 22688/73 and Helvetica Chimica Acta, 55, Fase 1, 224–239 (1972). On the other hand, chemical synthetic processes gave MPGA in the form of a racemic, D,L-mixture (Japanese Patent Prepublications Nos. 91019/73 and 139727/77).

We have studied on optical resolution of D,L-MPGA obtained by a chemical synthetic process and now found that N-acyl-D,L-MPGA can be optically resolved by a specific deacylation of N-acyl-L-MPGA with some acylases of microbial origin, so that L-MPGA can be isolated from N-acyl-D-MPGA.

BRIEF SUMMARY OF THE INVENTION

The present invention is based on the discovery that certain microbial acylases act as optically specific hydrolytic enzymes which are capable of selectively eliminating the acyl group of N-acylated-L-MPGA without affecting that of N-acyl-D-MPGA. Such microbial acylases are those produced by the cultivation of a strain of bacteria, the genus Pseudomonas, or of Actinomycetes, the genus Streptomyces or of fungi, the genus Aspergillus.

According to the present invention, therefore, there is provided a process for the optical resolution of D,L-2-amino-4-methylphosphinobutyric acid which comprises providing D,L-2-amino-4-methylphosphinobutyric acid in the form of its N-acyl derivative, reacting the N-acyl derivative in an aqueous medium with a microbial acylase having an optically specific hydrolytic activity which is produced by cultivating a microbial strain belonging to the genus Pseudomonas, Streptomyces or Aspergillus, whereby selectively eliminating the acyl group of N-acyl-L-2-amino-4-methylphosphinobutyric acid to give a mixture of L-2-amino-4-methylphosphinobutyric acid and N-acyl-D-2-amino-4-methylphosphinobutyric acid and isolating and recovering L-2-amino-4-methylphosphinobutyric acid from the mixture.

DETAILED DESCRIPTION OF THE INVENTION

The starting N-acyl-D,L-2-amino-4-methylphosphinobutyric acid is represented by the general formula:

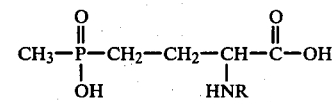

where R represents an unsubstituted or halo-substituted acyl group.

The acyl group of N-acyl-D,L-MPGA which serves as substrate for the microbial acylases we have found useful in the process of the present invention may be any of acyl groups so far as it is capable of being hydrolyzed with the action of the acylases to give L-MPGA. Usually, the acyl group may be selected from alkanoyl and aroyl groups, among which particularly preferred are alkanoyl groups having 1–5 carbon atoms such as formyl, acetyl, propionyl, butyryl and pentanoyl and benzoyl group. The acyl group may be halo-substituted so far as the halo-substituent or -substituents do not prevent the enzymatic reaction desired.

As typical examples of the microorganisms capable of producing a microbial acylase which is effective for the purpose of the present invention, there are mentioned:

Bacteria: *Pseudomonas maltophilia* BN-233 which was isolated by us from a soil sample collected at the peninsula Chita, Aichi Prefecture, Japan;

Actinomycetes: *Streptomyces violascens* SF-2072 and *Streptomyces diastatochromogenes* SF-2073, each of which was isolated by us from a soil sample collected at Shiga Prefecture, Japan;

Fungi: *Aspergillus* sp. KS-101 and *Aspergillus* sp. KS-102, each of which was isolated by us from a soil sample collected at Yokohama, Japan.

The above-mentioned strains each have the following microbiological characteristics:

*Pseudomonas maltophilia* BN-233

(a) Morphological properties

Cells grown on bouillon agar are of rod shape with a size of 0.5–0.7 microns by 1.0–2.0 microns and are motile by polar flagella. Neither the formation of spores nor polymorphism is observed. Gram-negative.

(b) Cultural properties on various culture media (1) Bouillon agar:

The cells grow with yellowish brown in color. The production of any diffusible pigment, wrinkled growth, gummy growth and swarming are not observed.

(2) Bouillon broth:

The whole of the culture medium becomes turbid. No pellicle is formed.

(3) Bouillon-gelatin stab:

The medium is liquefied.

(4) Milk:

The medium is liquefied with a pH changing into an alkaline range.

(c) Physiological properties:

(1) Reduction of nitrate: Negative (2) Denitrification: Negative (3) Methyl-red test: Negative
(4) Voges-Proskauer test: Negative
(5) Production of indole: Negative
(6) Production of hydrogen sulfide: Lead acetate paper is turned into black in color, but no blacking of TSI medium occurs.
(7) Hydrolysis of starch: Negative
(8) Utilization of citric acid: Positive
(9) Utilization of nitrogen source: The strain can use ammonium salt, but not use nitrate as sole nitrogen source.
(10) Production of water-soluble pigment on King A and B media: Not remarkable.
(11) Growth factors: Methionine is required.
(12) Accumulation of poly-$\beta$-hydroxybutyrate in the cells: Negative
(13) Oxidase test: Negative
(14) Temperature for growth: The strain grows at 15°–37° C., but does not grow at 5° C. and 42° C.
(15) Anaerobic condition: The strain cannot grow.
(16) O.F. test: O type
(17) Utilization of carbon source: The strain can use glucose, maltose, cellobiose and lactose as sole carbon source for growth, but cannot use glycerin and glutaric acid.

Identification of the strain BN-233 having the above-mentioned microbiological properties was carried out with reference to Bergey's Manual of Determinative Bacteriology, 8th edition (1974), resulting in the following conclusion:

(i) The BN-233 strain is deemed to belong to the genus Psedomonas in view that it is a gram-negative rod and motile by polar flagella and does not produce spores and that it is a strict aerobe.

(ii) The BN-233 strain is considered to belong to the species *Pseudomonas maltophilia* in view that it requires methionine, negative to oxidase test and positive to liquefaction of gelatin and also in view of its spectrum on carbon utilization.

Thus, we named the BN-233 strain as *Pseudomonas maltophilia* BN-233 and deposited the strain in a Japanese authorized depository, "Fermentation Research Institute, Agency of Industrial Science and Technology", Inage, Chiba-city, Japan, under deposit number FERM-P 4487 and also in the American Type Culture Collection, Washington, D.C., U.S.A., under deposit number ATCC. 31559.

*Streptomyces violascens* SF-2072

(a) Morphological properties

The formation of aerial mycelia is usually poor on various media, but is good on inorganic salts-starch-agar with abundant formation of spores. The aerial mycelia produce monopodial branches, no whorl-branching being observed. The tips of aerial mycelia are spiral (mainly compact spiral). No sclerotium is observed.

Electron-microscopic observation shows that the surface structure of the spores is spiny and that the spores are mainly of cylindrical shape with a size of 0.6–0.7 microns by 1.1–1.3 microns and usually form a chain comprising ten or more spores.

(b) Cultural properties on different culture media

The cultural properties of the strain SF-2072 are shown in Table 1 below, wherein the indication of colors given in a bracket [ ] is based on the standard of "Color Harmony Manual" made by Container Corporation of America. The incubation temperature was 28° C. and the observation was made after the incubation for 14–21 days.

Table 1

| Culture medium | Growth; color of reverse side | Aerial mycelium | Soluble pigment |
| --- | --- | --- | --- |
| Sucrose-nitrate agar | Poor growth, colorless | Very poor, cottony, pale lilac [llca] | None |
| Glucose-asparagine agar | Ordinary growth, light yellowish brown | None | None |
| Glycerol-asparagine agar | Ordinary growth, grayish yellow to light yellowish brown | None | None |
| Inorganic salts-starch agar | Good growth, light grayish yellow | Abundant, cottony, pale lilac [llca] | None |
| Oatmeal agar, | Ordinary growth, cream | Very poor, cottony, white | None |
| Yeast-malt agar | Ordinary or good growth, pale brown | None or very poor, white | None |
| Tyrosine agar | Ordinary or good growth, brown or dark brown | Very poor, cottony, white to pale lilac | Pale |
| Nutrient agar | ordinary growth, dark brown | None | Brown |

(c) Physiological properties (1) Growth temperature range:

The strain SF-2072 grows in a temperature range of 15°–38° C. on inorganic salts-starch agar. The optimum growth temperature is in a range of 25°–30° C.

(2) Liquefaction of gelatin:
Positive (at 20° C., 21 days incubation)

(3) Hydrolysis of starch:
Positive (at 28° C.)

(4) Coagulation of skimmed milk:
Negative (at 28° C.)

(5) Peptonization of skimmed milk:
Negative (at 28° C.)

(6) Production of melanin-like pigment:
Positive (d) Utilization of carbon sources (incubated on Pridham-Gottlieb's agar at 28° C.):

(i) Utilized: D-glucose, D-fructose, D-xylose, I-inositol, L-arabinose, sucrose, raffinose.

(ii) Not utilized: D-mannitol, rhamnose.

In view of the above-mentioned microbiological properties, the strain SF-2072 is estimated to belong to the genus Streptomyces. It produces aerial mycelia whose tips are in a spiral form. The spore surface has a spiny structure. The aerial mycelia assume pale lilac belonging to "Violet" series defined by Tresner H. D. and Bacus F. J. in Appl. Microbiol. 11, 355–338 (1963). The reverse side of the growth assumes pale yellowish brown without other distinct color. A melanin-like pigment is produced, but no production of other soluble pigment is observed.

Comparing the microbiological properties of the strain SF-2072 with those of *Streptomyces violascens* according to ISP (International Streptomyces Project) described in International Journal of Systematic Bacteriology, 18, 380–382 (1968), we found that the former substantially corresponds to the latter even to the minutest particulars and therefore designated the strain SF-2072 as *Streptomyces violascens* SF-2072.

This strain, *Streptomyces violascens* SF-2072 was deposited in Fermentation Research Institute, Japan, under deposit number FERM-P-4617 and also in the American Type Culture Collection, U.S.A., under ATCC. 31560.

*Streptomyces diastatochromogenes* SF-2073

(a) Morphological properties

The strain well produces aerial mycelia on inorganic salts-starch agar, oatmeal agar or tyrosine agar with abundant formation of spores. The aerial mycelia produce monopodial branches with no whorl-branching. The tips of aerial mycelia are spiral (mainly compact spiral). No sclerotium is observed.

Electron-microscopic view of the spores shows that they have a smooth surface and are of elliptical or short cylindrical shape with a size of 0.8–1.1 microns by 1.0×1.3 microns and usually form a chain comprising ten or more spores.

(b) Cultural properties on different culture media

The cultural properties of the strain SF-2073 are shown in Table 2 below. The incubation temperature was 28° C. and the observation was made after the incubation for 14–21 days.

Table 2

| Culture medium | Growth; color of reverse side | Aerial mycelium | Soluble pigment |
|---|---|---|---|
| Sucrose-nitrate agar | Ordinary or good growth, yellowish brown with gray tinge | Pale gray [2dc-2fe] | Faintly grayish yellow |
| Glucose-asparagine agar | Ordinary growth, pale brown | None or very poor, white | None |
| Glycerol-asparagine agar | Ordinary growth, pale gray | Poor, grayish white [2dc] | None |
| Inorganic salts-starch agar | Good growth, grayish brown | Abundant, brownish gray [3ge-4ig] | None |
| Oatmeal agar | Good growth grayish brown | Abundant, brownish gray [3ge] | None |
| Yeast-malt agar | Ordinary growth, pale brown | Poor, white to grayish white | None |
| Tyrosine agar | Good growth, dark brown to black | Abundant, brownish gray [3ge] | Dark brown |
| Nutrient agar | Ordinary growth, pale brown | None | Pale brown |

(c) Physiological properties (1) Growth temperature range:
The strain SF-2073 grows in a temperature range of 15°–38° C. on inorganic salts-starch agar. The optimum growth temperature is in a range of 25°–30° C.

(2) Liquefaction of gelatin:
Positive (at 20° C., 21 days incubation)

(3) Hydrolysis of starch:
Positive (at 28° C.)

(4) Coagulation of skimmed milk:
Negative (at 28° C.)

(5) Peptonization of skimmed milk:
Positive (at 28° C.)

(6) Production of melanin-like pigment:
Positive (d) Utilization of carbon sources (incubated on Pridham-Gottlieb's agar at 28° C.):

The strain well utilizes any of D-glucose, D-fructose, D-xylose, D-mannitol, L-arabinose, I-inositol, sucrose, raffinose and rhamnose for good growth.

In view of the above-mentioned microbiological properties, the strain SF-2073 is estimated to belong to the genus Streptomyces. The aerial mycelia are spiral at the tip thereof and the surface structure of the spores is smooth. The color of the aerial mycelia is brownish gray and the reverse side of the growth assumes pale brown to grayish brown without other distinct color. A melanin-like pigment is produced, but little or no production of other soluble pigment is observed.

Comparison of the microbiological properties of the strain SF-2073 with those of *Streptomyces diastatochromogenes* according to ISP described in International Journal of Systematic Bacteriology, 22, 290–294 (1972) showed a close resemblance therebetween. Thus, the strain SF-2073 was found to have microbiological properties corresponding most closely to those of *Streptomyces diastatochromogenes* among all the known strains classified under the genus Streptomyces, except such minor differences that in the strain SF-2073 the color at the reverse side of the growth on inorganic salts-starch agar or oatmeal agar is grayish brown and the tips of the aerial mycelia are substantially in spiral form, whereas in the ISP strain the color at the reverse side is pale yellow to grayish yellow and the tips of the aerial mycelia are not only in spiral form but also in wavy and straight forms.

Judging from the color resemblance in the fundamental properties of the SF-2073 strain to the ISP strain with some minor differences, we concluded to be most reasonable that the strain SF-2073 belongs to the species *Streptomyces diastatochromogenes* and designated it as *Streptomyces diastatochromogenes* SF-2073.

This strain was deposited in Fermentation Research Institute, Japan, under deposit number FERM-P 4618 and also deposited in the American Type Culture Collection, U.S.A., under ATCC No. 31561.

*Aspergillus* sp. KS-101

Incubation of the strain on potato starch-glucose agar at 28° C. for 10 days gives colonies having a diameter of 65 mm. The white mycelia produced are cottony, on which numerous, blackish brown spores are formed. Similar incubation of the strain on Czapek's agar gives colonies having a diameter of 70 mm, which assume velvet-like growth with a large number of blackish brown spores. On malt extract agar, the colonies formed have a diameter of 90 mm, wherein the mycelia are in short flocky form on which a great number of blackish brown spores are borne.

Under a microscopic observation, matured conidial heads are in globular shape with 40–60μ in diameter and densely bear blackish brown conidia. Conidiophores are smooth and have globular vesicles with 10–15μ in diameter at the tip thereof. Sterigmata are in two series and the conidia are in the form of globules of 3–4μ in diameter with numerous small verruca.

The strain well grows at a temperature range of 15°–37° C., but does not grow at 42° C.

Judging from the above-mentioned microbiological properties, we concluded that this strain belongs to the genus Aspergillus, and inter alia to the species *Aspergillus niger* and thus designated it as Aspergillus sp. KS-101.

This strain was deposited in Fermentation Research Institute, Japan, under deposit number FERM-P 4614 and also deposited in the American Type Culture Collection, U.S.A., under ATCC No. 20567.

*Aspergillus* sp. KS-102

Incubation of the strain on potato starch-glucose agar in a Petri dish at 28° C. for 10 days forms colonies with 13 mm in diameter growing in velvet-like appearance, the periphery of the colonies being white and the center slightly swelling and being yellowish green. Similar incubation of the strain on Czapek's agar gives colonies with 50 mm in diameter growing in deep green colored velvet-like appearance in which small black lumps with about 1 mm in diameter are sporadically formed. On malt extract agar, the colonies formed have a diameter of 90 mm growing in velvet-like appearance in which a great number of deep green spores are formed.

Under a microscopic observation, conidial heads are in clavate or columnar form and vesicles are in elliptical shape at an early growing age. At maturity, the conidial heads are in the form of globules with 40–60μ in diameter and the vesicles are also in globular or subglobular form with 15–20μ in diameter. The conidiophores are smooth, the sterigmata are in a single series and the conidia are in globular or subglobular shape with 4–6μ in diameter, the surface of which is smooth.

The strain well grows at a temperature range of 15°–40° C.

In view of the above-mentioned microbiological properties, we judged the strain to belong to the genus Aspergillus and inter alia to the species *Aspergillus flavor-oryzae* and designated it as Aspergillus sp. KS-102. This strain was deposited in Fermentation Research Institute, Japan, under deposit number FERM-P 4615 and also deposited in the American Type Culture Collection, U.S.A., under ATCC No. 20568.

All the strains above-mentioned have properties which are liable to vary as observed in known strains of a wide variety of microorganisms. Thus, the strains may produce variants or mutants when treated with various mutagens such as ultraviolet rays, X-rays, high-frequency electromagnetic waves, radioactive rays and chemicals. Therefore, any strain of the genera above-mentioned which includes any natural or artificial variant or mutant may be used for the purpose of the present invention so long as it is capable of producing a desired acylase.

The cultivation of an acylase-producing strain for the production of an acylase which is to be used as optically specific hydrolytic enzyme in the process of the optical resolution according to the present invention may be carried out in a known manner. Thus, an acylase-producing strain may be cultivated in a suitable culture medium containing nutrient sources which are utilizable by microorganisms in usual fermentation processes. As the nutrient sources, any of the known nutrients which have been used in the cultivation of ordinary microorganisms may be used. Thus, glucose, sucrose, starch, glycerin, malt syrup, molasses, vagetable oils and the like may be useful as carbon sources. Similarly, as useful nitrogen sources, there may be exemplified soybean meal, wheat germs, meat extract, peptone, corn steep liquor, dried yeast, ammonium nitrate, sodium nitrate and the like. If required, inorganic salts such as sodium chloride, potassium chloride, calcium carbonate, phosphates and the like and other additives which can promote the growth of the strain used whereby to accelerate the production of the desired acylase may be incorporated into the culture medium in any suitable combination thereof.

Liquid and solid culture methods conventionally used for the cultivation of usual microorganisms may be applied to the cultivation for the purpose of the present invention, a submerged culture being preferred for large scale operations. The cultivation is carried out under aerobic conditions at a temperature ranging 25°–37° C., most preferably at a temperature of around 28° C. The time of cultivation is of course dependent upon the cultivation conditions, particularly upon cultivation apparatus, composition of the culture medium, temperature, etc. Preferably, the cultivation may be continued until the activity of acylase produced reaches a maximum level. In most cases, the acylase-activity appears after one day from the start of cultivation, reaches a maximum level after two to three days and then lowers gradually and disappears. Usually, therefore, a period of 2–4 days will be suitable for the cultivation intended.

The culture thus obtained or "an enzyme material" derived from the culture by certain after-treatments thereof contains an acylase which acts as optically specific hydrolytic enzyme and can be used for the optical resolution according to the present invention. By the expression "an enzyme material" herein used is meant any desired form of materials obtained by subjecting the culture of the strains above-mentioned to a certain treatment or treatments suitable to transform the culture into a more advantageous form for the purpose of the enhancement in efficiency of the acyl-elimination by optically specific hydrolysis for the production of L-MPGA and N-acyl-D-MPGA. Thus, examples of said "enzyme material" include cells collected from the culture, either in a washed or unwashed form or in a dried or undried form, disintegrated cells, their extracts rich in the desired acylase which are derived by extraction of the ultrasonically or mechanically disintegrated cells followed by purification and immobilized acylase preparations derived from the cells, disintegrated cells or their extracts.

In carrying out the process of the present invention, the starting D,L-MPGA to be optically resolved is used in the form of its N-acyl derivative as already stated. The enzymatic deacylating reaction by optically specific hydrolysis of N-acyl-L-MPGA with the action of a microbial acylase is carried out in an aqueous medium. The reaction conditions should be chosen to make the best use of the properties of the acylase. If the acylase is used in the form of intact cells separated from the culture, the enzymatic activity thereof is satisfactorily high at a pH ranging 6–8.5 and lowers or disappears at a pH below 5 or above 9, no substantial difference in enzymatic properties being observed among acylases produced by different genera of microorganisms. The reaction temperature may be in the range of 20°–45° C. for any of acylases concerned, the most preferred range being 28°–35° C. Above 50° C., the acylases are observed to lose their activities.

Thus, the reaction conditions should preferably be at a pH ranging 6.5–8.5 and at a temperature ranging 25°–40° C. We have found that the microbial acylase to be used in the process of the present invention has little or a little activity on any of substrates other than N-acyl-L-MPGA, for example on N-acyl derivatives of known, usual L-amino acids.

In cases where the microbial acylase is used in the form of washed cells, it is preferred to disperse the cells in a solution of the substrate and to carry out the reaction in the dispersion. Effectively, the reaction is conducted with a suitable shaking or stirring. Alternatively, the reaction may be carried out by filling a column with the culture or an enzyme material derived therefrom and continuously passing the substrate solution through the column so that the deacylation occurs successively.

The time of reaction depends upon the concentration of substrate, degree of deacylating activity, reaction temperature and other factors and usually is in the range of 2–40 hours. The termination of the reaction may be determined by examining the time at which the production of the desired L-MPGA becomes maximum. The substrate concentration may be determined mainly in relation to the degree of deacylating activity and usually is in the range of 0.1–10%. If desired, any suitable antiseptic may be added to prevent any possible contamination of the reaction mixture with other microorganisms during the reaction.

The separation of L-MPGA and N-acyl-D-MPGA from the reaction mixture and the isolation and recovery of each of the compounds may be done in a known manner per se. Thus, the reaction mixture obtained may be subjected to filtration, centrifugal separation or any other separating operation to remove the cells or their derivative used. The filtrate or liquid fraction thus obtained may be passed through a column packed with an ion-exchange resin of a strongly acidic nature, e.g. "Dowex 50" (Dowex is a registered trade mark of Dow Chemical Company), where the L-MPGA is adsorbed on the column while the unreacted N-acyl-D-MPGA is passed through the column without being adsorbed. Then, the column may be developed with water to elute the L-MPGA which is positive to ninhydrin reaction and the eluate is purified, if necessary, by a treatment with an activated carbon or an ion-exchange resin, e.g. "Dowex 1" produced by Dow Chemical Company, and concentrated and crystallized or freeze-dried to give the pure L-MPGA in the form of crystals or white powder.

The fraction of N-acyl-D-MPGA already separated may be easily racemized in a known manner per se to give a further amount of the starting N-acyl-D,L-MPGA. Thus, for example, the fraction of N-acyl-D-MPGA may be dissolved in an aqueous sodium hydroxide and the resulting solution may be racemized by the addition of a large excess amount of acetic anhydride or by passing a ketene gas through the solution. Alternatively, the racemization of N-acyl-D-MPGA may be effected by maintaining N-acyl-D-MPGA in glacial acetic acid and adding an equimolar or less proportion of acetic anhydride thereto under heating. A number of repeat of the process of the optical resolution according to the present invention in combination with the subsequent racemization will result in the complete transformation of D-MPGA into L-MPGA.

The completion of the enzymatic deacylation may be determined by measuring the amount of L-MPGA formed by the following method:

The amount of L-MPGA formed can be quantitatively determined by spectrophotometry using ninhydrin as reagent wherein a standard calibration curve is first prepared, with which the absorbancy of a sample tested is compared [see E. W. Yemm and E. C. Cocking, Analyst, 80, 209 (1955)].

Reagents:
Solution A: A 4 M acetic acid buffer solution (pH: 5.0);
Solution B: A mixture of 5 ml of 0.01 M potassium cyanide solution with 245 ml of methyl cellosolve;
Solution C: A solution of 2.5 g of ninhydrin in 50 ml of methyl cellosolve;
Solution D: A mixture of 250 ml of Solution B and 50 ml of Solution C;
Solution E: A 60% ethanol solution;
Measuring procedure:

A 1.0 ml aliquot of a sample solution to be tested is taken in a test tube, to which are added 0.5 ml of Solution A and 1.2 ml of Solution D. The resulting mixture is kept in a boiling water bath for 15 minutes and then cooled in cold water for 5 minutes. Then, a 3.0 ml aliquot of Solution E is added to the mixture and the resulting solution is well stirred and measured its absorbancy at 570 nm on a spectrophotometer.

The standard curve of absorbancy of L-MPGA shows a straight relation in the concentrations ranging from 1 to 50 $\mu$g/ml, so that the comparison of the values measured with the standard curve gives the content of L-MPGA in the sample solution.

The following Examples further illustrate some typical embodiments of the present invention.

EXAMPLE 1

A loopful amount of a slant culture of *Pseudomonas maltophilia* BN-233 (FERM-P 4487) was inoculated to 200 ml of a sterilized culture medium containing 0.5% glucose, 0.3% meat extract, 0.5% peptone, 0.2% sodium glutamate, 0.001% cobalt chloride and 0.001% ferrous sulfate. The inoculated medium was cultured with shaking at 28° C. for 42 hours. The culture broth was centrifuged at 8000 rpm for 20 minutes to collect the cells which were then washed with 50 ml physiological salt solution to give 5 g(wet weight) of the washed cells.

A 1.6 g portion of the washed cells was suspended in 50 ml of a 0.05 M phosphate buffer solution (pH 5), to which was then added 240 mg of N-acetyl-D,L-MPGA and the mixture was maintained in a 200 ml Erlenmeyer flask at 28° C. under shaking for 18 hours to complete the reaction. Thereafter, the reaction mixture was centrifuged to give a solid mass comprising the cells and a supernatant liquid. The solid mass was washed twice with 5 ml portions of water and the washings were combined with the supernatant liquid. The combined liquid was passed through a column (1.6 cm in diameter and 12 cm in height) of an ion exchange resin "Dowex 1×2" ($CH_3COO^-$), through which were passed a large amount of water for washing and then an amount of 0.3 N acetic acid as developer. The eluate fractions (total volume: 90 ml) which were positive to ninhydrin reaction were collected together, concentrated to dryness under a reduced pressure and freeze-dried to yield 84 mg of L-MPGA as white powder. Purity 85%, $[\alpha]_D^{22}$ 21.7° (c=1, 1 N HCl), Yield 68%.

EXAMPLE 2

A loopful amount of a slant culture of *Streptomyces violascens* SF-2072 (FERM-P 4617) was inoculated to 200 ml of a sterilized culture medium containing 1% soluble starch, 0.2% yeast extract and 0.2% peptone (pH 7.0 before sterilization). The inoculated medium was cultured with shaking at 28° C. for 72 hours. The resulting culture was suction-filtered using a filter paper of "Toyo No. 2" and the cells collected on the paper were washed with 50 ml of physiological salt solution to give 6.5 g (wet weight) of the washed cells.

A 3 g portion of the washed cells was thoroughly suspended in 200 ml of a 0.05 M phosphate buffer solution (pH 7.0). To the suspension was added 400 mg of N-acetyl-D,L-MPGA and the mixture was maintained at 30° C. under shaking for 16 hours to complete the reaction. Then, the reaction mixture was filtered through a filter paper of "Toyo No. 2" and the solid mass collected on the paper was washed with 20 ml of water. The filtrate and the washing were combined together and the mixture was passed through a column (1.2 cm in diameter and 15 cm in height) of an ion exchange resin "Dowex 50×2" (H+), through which was then passed an amount of water as developer. Eluate fractions (total volume: 160 ml) which were positive to ninhydrin reaction were collected together, concentrated to dryness under a reduced pressure and freeze-dried to yield 158 mg of L-MPGA as white powder. Purity 92%, $[\alpha]_D^{22}$ 23° (c=1, 1 N HCl), Yield 88.6%.

EXAMPLE 3

The eluate fractions which have passed through the column of Dowex 50×2 (H+) in Example 2 were collected together, the total volume of which amounting to 250 ml, neutralized with 1 N sodium hydroxide solution and concentrated to dryness under a reduced pressure. To the dried concentrate were added 2 ml of acetic acid and 0.11 ml of acetic anhydride and the mixture was refluxed at 100° C. for 18 hours. The resulting mixture was concentrated to dryness under a reduced pressure and the solid residue was subjected to enzymatic deacetylation in the same manner as used in Example 2, yielding 55 mg of L-MPGA as white powder. $[\alpha]_D^{22}$ 22° (c=1, 1 N HCl).

EXAMPLE 4

The following strains were used for the cultivation for the production of the desired microbial acylases in the same manner as described in the preceding Examples.

A: *Psudomonas maltophilia* BN-233 (FERM-P 4487)
B: *Streptomyces violascens* SF-2072 (FERM-P 4617)
C: *Streptomyces diastatochromogenes* SF-2073 (FERM-P 4618)
D: *Aspergillus* sp. KS-101 (FERM-P 4614)
E: *Aspergillus* sp. KS-102 (FERM-P 4615)

A 100 mg (wet weight) portion of each of the washed cells produced by the cultivation of the above-mentioned strains was suspended in 1 ml of a 0.05 M phosphate buffer solution (pH 7.0) and to the suspension was added 5 mg of each of the substrates given in the following table and the mixture was maintained in a tube shaker at 28° C. for 6 hours to complete the reaction. The reaction mixture was after-treated as in the preceding Examples and the percent production of L-MPGA was measured by a spectrophotometry on each of the filtrates using ninhydrin as reagent. The results are given in the following table.

Table

| Substrate | Percent production of L-MPGA | | | | |
|---|---|---|---|---|---|
| | A | B | C | D | E |
| N-acetyl-L-MPGA | 55.0 | 73.2 | 65.4 | 52.0 | 45.8 |
| N-propionyl-L-MPGA | 52.2 | 70.5 | 55.0 | 38.0 | 46.2 |
| N-butyryl-L-MPGA | 38.8 | 46.4 | 46.4 | 37.5 | 35.0 |
| N-benzoyl-L-MPGA | 24.3 | 36.1 | 26.1 | 24.0 | 22.4 |
| N-p-chlorobenzoyl-L-MPGA | 21.6 | 33.8 | 24.5 | — | 18.6 |

Details of the production of washed cells:
Strain A: Similar to the method of Example 1
Strains B and C: Similar to the method of Example 2
Strains D and E: Shake-cultivated on a sterilized culture medium containing 1% peptone, 0.2% yeast extract, 2% glucose and 0.001% cobalt chloride (pH 7.0 before sterilization) at 28° C. for 68 hours. The resulting culture was filtered and washed to yield the washed cells.

EXAMPLE 5

A 3 g portion of the washed cells of *Streptomyces violascens* SF-2072 (FERM-P 4617) obtained in Example 2 was suspended in 100 ml of a 0.05 M phosphate buffer solution (pH 7.0). The resulting suspension was subjected to cell-disintegration treatment on a French pressure cell under a pressure of 1500 psi and then centrifuged at 1500 rpm. The supernatant liquid obtained was used as acylase in the following experiment.

A 20 ml portion of the acylase was mixed with 120 mg of N-acetyl-D,L-MPGA and the mixture was maintained at 30° C. for 16 hours to complete the reaction. Then, the reaction mixture was passed through a column (1.2 cm in diameter and 10 cm in height) of an ion exchange resin "Dowex 50×2" (H+), through which was then passed an amount of water as developer. Eluate fractions which were positive to ninhydrin reaction were collected, the total volume of which amounting to 24 ml, treated with 100 mg of activated carbon at room temperature with stirring for 30 minutes and filtered. The carbon filtered off was washed twice with 5 ml portions of water. The filtrate was combined with the washings and the combined liquid was concentrated to dryness under a reduced pressure and then freeze-dried to yield 48 mg of L-MPGA as white powder. Purity 91%, $[\alpha]_D^{22}$ 21.5° (c=1, 1 N HCl), Yield 88.7%.

EXAMPLE 6

A 50 ml portion of the acylase obtained in Example 5 was adjusted to pH 5.5 with the addition of 1 N HCl, to which was then added 20 ml of DEAE-Sephacel (OH type, Sephacel is registered trade mark to Pharmacia) which had been well swollen with water and the mixture was stirred at 5° C. for 3 hours to make complete the adsorption of the acylase on the DEAE-Sephacel. The mixture was then centrifuged at 3000 rpm for 20 minutes to separate the DEAE-Sephacel in a gel state, which was then washed twice with 50 ml portions of a 0.05 M phosphate buffer solution (pH 7.0). A solution of 50 mg of N-acetyl-D,L-MPGA in 50 ml of a 0.05 M phosphate buffer solution (pH 7.0) was added to 10 ml of the DEAE-Sephacel gel so obtained and the mixture was stirred with a magnetic stirrer at 30° C. for 16 hours to complete the reaction. The reaction mixture was centrifuged at 3000 rpm for 20 minutes to separate the DEAE-Sephacel gel, which was then washed with 5 ml of the same buffer solution. The supernatant liquid from the centrifuge was combined with the washing.

The same reaction as above was repeated by adding 50 ml of a 0.1% N-acetyl-D,L-MPGA-phosphate buffer solution to the washed DEAE-Sephacel gel. The percent production of L-MPGA was measured by a spectrophotometry on the supernatant liquid from the reaction using ninhydrin as reagent.

The reaction was carried out three times in all with the same DEAE-Sephacel-acylase gel, the results of which are shown below with respect to the percent production of L-MPGA.
1st run: 86.1%
2nd run: 85.0%
3rd run: 81.2%

What we claim is:
1. A process for the optical resolution of D,L-2-amino-4-methylphosphinobutyric acid which comprises the steps of:

providing D,L-2-amino-4-methylphosphinobutyric acid in the form of its N-acyl derivative;

reacting the N-acyl derivative of D,L-2-amino-4-methylphosphinobutyric acid in an aqueous medium with a microbial acylase having an optically specific hydrolytic activity which is produced by cultivating a microbial strain belonging to the genus Pseudomonas, Streptomyces or Aspergillus; whereby selectively eliminating the acyl group of N-acyl-L-2-amino-4-methylphosphinobutyric acid to give a mixture of L-2-amino-4-methylphosphinobutyric acid and N-acyl-D-2-amino-4-methylphosphinobutyric acid; and isolating and recovering L-2-amino-4-methylphosphinobutyric acid from the mixture.

2. A process according to claim 1 wherein the microbial strain is a strain of the species *Pseudomonas maltophilia*.

3. A process according to claim 2 wherein the strain is *Pseudomonas maltophilia* BN-233 identified as FERM-P 4487 or ATCC No. 31559.

4. A process according to claim 1 wherein the microbial strain is a strain of the species *Streptomyces violascens*.

5. A process according to claim 4 wherein the strain is *Streptomyces violascens* SF-2072 identified as FERM-P 4617 and ATCC No. 31560.

6. A process according to claim 1 wherein the microbial strain is a strain of the species *Streptomyces diastatochromogenes*.

7. A process according to claim 6 wherein the strain is *Streptomyces diastatochromogenes* SF-2073 identified as FERM-P 4618 and ATCC No. 31561.

8. A process according to claim 1 wherein the microbial strain is a strain of the species *Aspergillus niger*.

9. A process according to claim 8 wherein the strain is Aspergillus sp. KS-101 identified as FERM-P 4614 and ATCC No. 20567.

10. A process according to claim 1 wherein the microbial strain is a strain of the species *Aspergillus flavus-oryzae*.

11. A process according to claim 10 wherein the strain is Aspergillus sp. KS-102 identified as FERM-P 4615 and ATCC No. 20568.

12. A process according to claim 1 wherein the microbial acylase is used in the form of a culture obtained by the cultivation of a microbial strain stated or an enzyme material derived from the culture by an after-treatment thereof.

13. A process according to claim 12 wherein the enzyme material is cells collected from the culture in a washed or unwashed form or a dried or undried form, disintegrated cells, their extracts rich in the microbial acylase which are derived by extraction of the disintegrated cells followed by purification or immobilized acylase preparations derived from the cells, disintegrated cells or their extracts.

14. A process according to claim 1 wherein the microbial acylase is produced by the cultivation of a microbial strain stated under aerobic conditions in a suitable culture medium at a temperature of 25°–37° C. for a period of time at which the activity of acylase produced reaches a maximum level.

15. A process according to claim 1 wherein the unreacted N-acyl-D-2-amino-4-methylphosphinobutyric acid is recovered from the reaction mixture and racemized in a known manner to produce a further amount of N-acyl-D,L-2-amino-4-methylphosphinobutyric acid for recycling to the reaction with the microbial acylase.

* * * * *

UNITED STATES PATENT AND TRADEMARK OFFICE
CERTIFICATE OF CORRECTION

PATENT NO. : 4,226,941
DATED : October 7, 1980
INVENTOR(S) : GOI et al

It is certified that error appears in the above-identified patent and that said Letters Patent are hereby corrected as shown below:

In the title page, column 1, in the title, change "D,L-2-Amino-4-methylphosphinobutryric acid" to --D,L-2-Amino-4-hydroxy(methyl phosphinoylbutyric acid--. Title page, column 2, in the abstract, line 1, change "L-2-Amino-4-methylphosphinobutyric acid" to --L-2-Amino-4-hydroxy(methyl)phosphinoylbutyric acid--. Column 1, in the title of the invention, lines 3-4, change "D,L-2-Amino-4-Methylphosphinobutyric acid" to D,L-2-Amino-4-hydroxy(methyl)phosphinoylbutyric acid. Lines 9-10 (i.e. lines 2-3 after "Summary of the Invention") change "D,L-2-amino-4-methylphosphinobutyric acid" to D,L-2-amino-4-hydroxy(methyl)phosphinoylbutyric acid--. Lines 10-11, change"L-2-amino-4-methylphosphinobutyric acid" to --L-2-amino-4-hydroxy(methyl)phosphinoylbutyric acid--. Line 13, change "D,L-2-amino-4-methylphosphinobutyric acid" to --D,L-2-amino-4-hydroxy(methyl)phosphinoylbutyric acid--. Lines 57-58, change "D,L-2-amino-4-methylphosphinobutyric acid" to --D,L-2-amino-4-hydroxy(methyl)

UNITED STATES PATENT AND TRADEMARK OFFICE
CERTIFICATE OF CORRECTION

PATENT NO. : 4,226,941
DATED : October 7, 1980
INVENTOR(S) : GOI et al

It is certified that error appears in the above-identified patent and that said Letters Patent are hereby corrected as shown below:

phosphinoylbutyric acid--. Line 59-60, change "D,L-2-amino-4-methylphosphinobutyric acid" to --D,L-2-amino-4-hydroxy(methyl)phosphinoylbutyric acid--. Lines 66-67, change "N-acyl-L-2-amino-4-methylphosphinobutyric acid" to --N-acyl-L-2-amino-4-hydroxy(methyl)phosphinoylbutyric acid--. Lines 67-68, change "L-2-amino-4-methylphosphinobutyric acid" to --L-2-amino-4-hydroxy(methyl)phosphinoylbutyric acid--. Column 1, line 68 and column 2, line 1, change "N-acyl-D-2-amino-4-methylphosphinobutyric acid" to --N-acyl-D-2-amino-4-hydroxy(methyl)phosphinoylbutyric acid--. Column 2, line 2, change "L-2-amino-4-methylphosphinobutyric acid" to --L-2-amino-4-hydroxy(methyl)phosphinoylbutyric acid--. Lines 7-8, (i.e. lines 1-2 after "Detailed Description of the Invention") change "N-acyl-D,L-2-amino-4-methylphosphinobutyric acid" to --N-acyl-D,L-2-amino-4-hydroxy(methyl)phosphinoylbutyric acid--. Column 12, lines 66-67, change "D,L-2-amino-4-methylphosphinobutyric acid" to

UNITED STATES PATENT AND TRADEMARK OFFICE
CERTIFICATE OF CORRECTION

PATENT NO. : 4,226,941   Page 3 of 4
DATED : October 7, 1980
INVENTOR(S) : GOI et al It is certified that error appears in the above-identified patent and that said Letters Patent are hereby corrected as shown below:

--D,L-2-amino-4-hydroxy(methyl)phosphinoylbutyric acid--. Column 13, lines 1-2, change "D,L-2-amino-4-methylphosphinobutyric acid" to --D,L-2-amino-4-hydroxy(methyl)phosphinoylbutyric acid--. Lines 3-4, change "D,L-2-amino-4-methylphosphinobutyric acid" to --D,L-2-amino-4-hydroxy(methyl)phosphinoylbutyric acid--. Lines 10-11, change "N-acyl-L-2-amino-4-methylphosphinobutyric acid" to --N-acyl-L-2-amino-4-hydroxy(methyl)phosphinoylbutyric acid--. Lines 12-13, change "L-2-amino-4-methylphosphinobutyric acid" to --L-2-amino-4-hydroxy(methyl)phosphinoylbutyric acid--. Lines 13-14, change "N-acyl-D-2-amino-4-methylphosphinobutyric acid" to --N-acyl-D-2-amino-4-hydroxy(methyl)phosphinoylbutyric acid--. Lines 15-16, change "L-2-amino-4-methylphosphinobutyric acid" to --L-2-amino-4-hydroxy(methyl)phosphinoylbutyric acid--. Column 14, lines 32-33, change "N-acyl-D-2-amino-4-methylphosphinobutyric acid" to --N-acyl-D-2-amino-4-hydroxy(methyl)phosphinoylbutyric acid--.

UNITED STATES PATENT AND TRADEMARK OFFICE
CERTIFICATE OF CORRECTION

PATENT NO. : 4,226,941
DATED : October 7, 1980
INVENTOR(S) : GOI et al

It is certified that error appears in the above-identified patent and that said Letters Patent are hereby corrected as shown below:

Column 14, line 35, change "N-acyl-D,L-2-amino-4-methylphosphino-butyric acid" to --N-acyl-D,L-2-amino-4-hydroxy(methyl)phosphino-ylbutyric acid--.

Signed and Sealed this

Twenty-ninth Day of September 1981

[SEAL]

Attest:

Attesting Officer

GERALD J. MOSSINGHOFF

Commissioner of Patents and Trademarks